United States Patent [19]
Chung et al.

[11] Patent Number: 5,945,574
[45] Date of Patent: *Aug. 31, 1999

[54] OLEFIN OLIGOMERIZATION PROCESS AND CATALYSTS THEREFOR

[75] Inventors: Tze-Chiang Chung; Ruidong Ding, both of State College, Pa.; Ronald L. Shubkin, Baton Rouge, La.

[73] Assignee: BP Amoco Corporation, Chicago, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 08/572,224

[22] Filed: Dec. 13, 1995

[51] Int. Cl.[6] .............................. C07C 2/26; C07C 2/28; C07C 2/32

[52] U.S. Cl. ..................... 585/511; 585/510; 585/517; 585/520; 585/521; 585/530

[58] Field of Search .................................. 585/510, 511, 585/517, 520, 521, 530; 502/150, 152, 153, 154, 159

[56] References Cited

U.S. PATENT DOCUMENTS

| | | | |
|---|---|---|---|
| 4,329,252 | 5/1982 | Gavens et al. | 526/129 |
| 4,734,472 | 3/1988 | Chung | 526/239 |
| 4,751,276 | 6/1988 | Chung | 526/158 |
| 5,288,677 | 2/1994 | Chung et al. | 502/152 |

*Primary Examiner*—Elizabeth D Wood
*Attorney, Agent, or Firm*—James R. Henes; Stephen L. Hensley

[57] ABSTRACT

The use of novel heterogeneous catalyst complexes as catalysts for oligomerizing alpha-olefins is disclosed. The complexes are formed from (i) a solid olefin polymer having a linear backbone and a plurality of pendant omega-hydroxyalkyl groups, (ii) an organomagnesium halide, and (iii) a boron trihalide, preferably $BF_3$. The complexes can be recovered and reused repeatedly in batch-type operations and can be used for long periods of time in continuous or semi-continuous operations without replenishment of their boron trifluoride content.

20 Claims, No Drawings

OLEFIN OLIGOMERIZATION PROCESS AND CATALYSTS THEREFOR

TECHNICAL FIELD

This invention relates generally to the preparation of alpha-olefin oligomers which are useful as synthetic lubricants and functional fluids, and particularly to a novel catalyst system and a novel catalytic process for conducting such oligomerizations.

BACKGROUND

Alpha-olefin oligomers and their use as synthetic lubricants are well-known. The oligomers are usually hydrogenated in order to improve their stability. Hydrogenated oligomers produced from 1-alkenes, especially linear 1-alkenes, having in the range of about 8 to about 14 carbon atoms are generally deemed most suitable for use as synthetic lubricants and fluids. Hydrogenated oligomer oils with viscosities of about 2–10 cSt at 100° C. are typically used for general lubricating oil applications. These materials are, in general, mixtures of different percentages of dimer, trimer, tetramer, pentamer and, in the case of the higher viscosity products in this range, higher oligomers as well. For some lubricant applications, hydrogenated oligomers with still higher viscosities are desired.

While various types of alpha-olefin oligomerization catalysts have been disclosed, catalysts based on boron trifluoride have proven most useful. Patent literature on $BF_3$-based alpha-olefin oligomerization includes U.S. Pat. Nos. 2,806,072; 3,149,178; 3,382,291; 3,769,363; 3,997,621; 4,172,855; 4,218,330; 4,436,947; 4,982,026; 5,068,487; 5,191,140; 5,396,013; and 5,420,373. As indicated in these disclosures, a suitable promoter is used with the $BF_3$ to render it suitably effective for effecting the oligomerization.

Although the boron trifluoride-based catalyst systems exemplified by the above patents are effective, they are not without drawbacks or deficiencies. Chief among these are the problems of recovery and disposal of the catalyst residues. See for example U.S. Pat. Nos. 4,213,001; 4,263,467; 4,308,414; 4,384,162; 4,394,296; 4,433,197; 4,454,366; and 4,981,578 which describe various ways of coping with these problems.

U.S. Pat. No. 5,288,677 discloses immobilized Lewis acid catalysts and their use as catalysts for the polymerization of isobutylene, mixed butenes and copolymerization of monomers including 1-butene, ethylene and 1-hexene. One of the catalysts used for polymerization of isobutylene is hydroxylated polybutene-1 copolymer which has been reacted with $BF_3$ in a manner to form a sigma (σ) bond between the oxygen and the boron atoms. For ease of description this copolymer is depicted in simplified form in the patent as PB—O—$BF_2$ ("PB" referring to polybutene). Additional experiments have been conducted using PP—O—$BF_2$ catalyst systems, such as:

PP—O—$BF_2$/n-BuOH;
PP—O—$BF_2$/n-BuOH/$CH_2Cl_2$;
PP—O—$BF_2$/HCl;
PP—O—$BF_2$/HCl/$CH_2Cl_2$;
PP—O—$BF_2$/HCl;
PP—O—$BF_2$/t-BuCl; and
PP—O—$BF_2$/$BF_3$ (gaseous $BF_3$)

where "PP" refers to polypropylene, n-BuOH is n-butanol, $CH_2Cl_2$ is methylene chloride, and t-BuCl is tertiary butyl chloride, and where the $BF_3$ was in gaseous form. This work has shown that all of these additional systems show good reactivity in polymerizing isobutylene and styrene. Unfortunately, all of these systems showed no reactivity to 1-octene.

U.S. Pat. No. 5,811,617 assigned to the same assignee as this application by unrecorded assignment, discloses a catalytic process for oligomerizing a 1-olefin. In that process the catalyst system used is formed from (i) a solid olefin polymer having a linear backbone and a plurality of pendant omega-hydroxyalkyl groups, and (ii) a boron trihalide, most preferably boron trifluoride. One important advantage of that catalyst system is that the solid polymer of the heterogeneous catalyst system can be readily recovered and reused repeatedly in batch-type operations and can be used for long periods of time in continuous or semi-continuous operations. However, that catalyst system does require periodic replenishment with the boron trihalide such as by bubbling boron trifluoride into a slurry composed of the solid polymer catalyst component from a previous run and a fresh charge of 1-olefin. It would be desirable to eliminate, or at least substantially reduce, the need for such periodic replenishment of the heterogeneous catalyst polymeric residue with the boron trihalide. The present invention has achieved this goal.

SUMMARY OF THE INVENTION

This invention in one of its embodiments provides a new heterogeneous catalyst system formed from (i) a solid olefin polymer having a linear backbone and a plurality of pendant omega-hydroxyalkyl groups, (ii) an organomagnesium halide, and (iii) a boron trihalide, most preferably boron trifluoride. The available chemical evidence supports the view that the unification of these components results in the formation under ordinary ambient room temperature conditions of a novel complex which, using polypropylene having a plurality of pendant substituents as a typical example, may be depicted as follows:

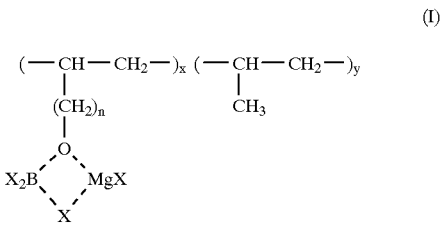

(I)

where X is halide, x is an integer representing the number of the substituted polypropylene units in the molecule, y is an integer representing the number of unsubstituted polypropylene units in the molecule, and n is an integer representing the length of the carbon chain of the pendant substituents.

Another embodiment of this invention is a novel catalytic process for producing 1-olefin oligomers which utilizes a stable heterogeneous catalyst system involving boron trihalide that is very reactive at relatively high temperatures, that is readily recoverable and reusable in further oligomerization reactions, and that does not require frequent replenishment with boron trihalide. In accordance with this embodiment, a 1-olefin having in the range of about 6 to about 20, and preferably in the range of about 8 to about 14 carbon atoms, or a mixture of two or more such 1-olefins, is oligomerized by contact with a catalyst system formed from (i) a solid olefin polymer having a linear backbone and a plurality of pendant omega-hydroxyalkyl groups, (ii) an organomagnesium halide, and (iii) a boron trihalide, most preferably boron trifluoride. Oligomerization proceeds readily in short reaction periods and at convenient reaction temperatures, including room temperature.

The catalyst system or complex of this invention is readily prepared by combining a Grignard reagent with a solid olefin polymer having pendant omega-hydroxyalkyl groups and then combining a boron trihalide, preferably boron trifluoride, with the resultant product. Both steps are preferably conducted in a suitable anhydrous medium, such as a hydrocarbon diluent, under an inert atmosphere, using the substituted olefin polymer in finely-divided or particulate form. Both steps can be conducted at room temperature. The process for producing the catalyst system or complex forms still another embodiment of this invention.

The catalyst systems or complexes of this invention can be recovered and reused repeatedly in batch-type operations and can be used for long periods of time in continuous or semi-continuous operations. Thus in a batch-type process, the solid catalyst material can be readily separated from the liquid oligomerization product mixture by filtration or like physical separation procedure, and used in ensuing operations. All that is necessary is to keep the catalyst material in an anhydrous inert environment when not in use. In continuous and semi-continuous operations the solid catalyst system can be used as a bed through which the olefin is passed.

The above and other embodiments and features of this invention will become still further apparent from the ensuing description and appended claims.

FURTHER DESCRIPTION

Olefins for Oligomerization

The olefins used in making the oligomers are predominately (at least 50 mol %) $C_6$–$C_{20}$ and preferably predominately $C_8$–$C_{14}$ straight chain (i.e., linear) monoolefinically unsaturated hydrocarbons in which the olefinic unsaturation exists in the 1- or alpha-position of the straight chain. Such alpha-olefins are available as articles of commerce, and can be made by thermal cracking of paraffinic hydrocarbons or by well-known Ziegler ethylene chain growth technology. Individual olefins can be used as well as mixtures of such olefins. Examples of olefins that can be used are 1-hexene, 1-heptene, 1-octene, 1-nonene, 1-decene, 1-undecene, 1-dodecene, 1-tridecene, 1-tetradecene, 1-hexadecene, 1-octadecene, 1-eicosene, and mixtures of two or more of such 1-olefins. Remotely branched 1-olefins such as 5-methyl-1-heptene, 6-methyl-1-heptene, 6-methyl-1-octene, 7-methyl-1-octene, 6,7-dimethyl-1-octene, 7,7-dimethyl-1-octene, 8-methyl-1-nonene, and like 1-olefins can also be used especially when used together with linear 1-olefins. The most preferred 1-olefin monomers are 1-octene, 1-decene, 1-dodecene and mixtures of any two or all three of these.

Minor amounts of up to about 50, and usually less than 25 mol % of internal and/or vinylidene olefins can be present in the olefin monomers.

The oligomerizable olefins used in the practice of this invention can also be mixtures or combinations of olefins having an average in the range of about 6 to about 20 carbon atoms per molecule, such as mixtures of butenes, hexenes, octenes, decenes and dodecenes having an average carbon content per molecule falling in this range.

Olefin Polymer with Pendant Omega-Hydroxyalkyl Groups

The olefin polymer having pendant omega-hydroxyalkyl groups can be prepared in a two-stage operation. In the first stage a polymer having hydrocarbyl-borohydrocarbyl groups depending from the backbone is formed. This involves either homopolymerizing or copolymerizing a hydrocarbyl borane monomer having an omega-alkenyl group (e.g., B-(5-hexen-1-yl)-9-BBN, B-(7-octen-1-yl)-9-BBN, etc.) as described for example in U.S. Pat. Nos. 4,734,472 and 4,751,276. The polymerization is effected using a suitable Ziegler-Natta catalyst system such as $TiCl_3AA/AlEt_2Cl$ (where "AA" means alumina activated). Procedures for producing the hydrocarbylborane monomers are also described in these two patents. When forming the copolymers, the hydrocarbyl borane having an omega-alkenyl group is copolymerized with at least one straight chain 1-olefin, preferably a straight chain 1-olefin having 3–10 (more preferably 3–6) carbon atoms or a mixture of any two or more of these, most preferably propylene. The copolymers formed in this first stage may contain from 0.1 to 99.9 mol % of units derived from the hydrocarbyl borane monomer and from 99.9 to 0.1 mol % of units derived from the straight chain 1-olefin(s). Preferred copolymers have from about 1 to about 15 mol % of units derived from the hydrocarbyl borane monomer and from about 99 to about 85 mol % of units derived from the straight chain 1-olefin(s).

In the second stage the hydrocarbylborane-substituted polymer formed in the first stage is reacted with an inorganic base and a peroxide, preferably sodium hydroxide and hydrogen peroxide, to form the olefin polymer having pendant omega-hydroxyalkyl groups. Once again U.S. Pat. Nos. 4,734,472 and 4,751,276 provide a detailed description of this synthesis procedure.

Suitable olefin polymers having pendant omega-hydroxyalkyl groups comprise poly(1-alken-$\overline{\omega}$-ol) polymers in which the 1-alken-$\overline{\omega}$-ol units contain 6 to about 12 carbon atoms each, and poly(1-alkene-co-1-alken-$\overline{\omega}$-ol) polymers in which the alkene units contain 3 to about 10 carbon atoms each and the 1-alken-$\overline{\omega}$-ol units contain 6 to about 12 carbon atoms each. The homopolymers are typified by poly(1-hexen-6-ol) and poly(1-octen-8-ol). The copolymers include poly(1-butene-co-1-alken-$\overline{\omega}$-ol) polymers, such as poly(1-butene-co-1-hexen-6-ol) and poly(1-butene-co-1-octen-8-ol); poly(1-pentene-co-1-alken-$\overline{\omega}$-ol) polymers, such as poly (1-pentene-co-1-hexen-6-ol) and poly(1-pentene-co-1-hepten-7-ol); and poly(1-hexene-co-1-alken-$\overline{\omega}$-ol) polymers, such as poly(1-hexene-co-1-hexen-6-ol) and poly (1-hexene-co-1-decen-10-ol). Particularly preferred olefin polymers having pendant omega-hydroxyalkyl groups are poly(propylene-co-1-alken-$\overline{\omega}$-ol) polymers, such as poly (propylene-co-1-hexen-6-ol), poly(propylene-co-1-hepten-7-ol), poly(propylene-co-1-octen-8-ol), poly(propylene-co-1-nonen-9-ol), and poly(propylene-co-1-decen-10-ol). These propylene-derived copolymers are when suitably prepared have crystallinity and brush-like molecular structures with the hydroxyl groups at the ends of flexible side chains. Note in this connection, T. C. Chung, *Polymer News*, 1993, Volume 18, pages 38–43 and *Chemtech*, 1991, Volume 21, pages 496–499. Thus they are capable of forming highly active catalytic complexes of this invention. Poly (propylene-co-1-hexen-6-ol) is a particularly preferred hydroxyalkyl olefin polymer for use in forming the catalysts of this invention.

Catalyst Systems or Complexes

To form the catalysts of this invention the olefin polymer having pendant omega-hydroxyalkyl groups is first reacted with an organomagnesium compound, preferably an organomagnesium halide, commonly known as a Grignard reagent. The olefin polymer is preferably treated in a particulate or finely-divided state while suspended in an anhydrous inert medium such a paraffinic, cycloparaffinic or aromatic hydrocarbon, and under an inert atmosphere. The treatment is normally conducted at ordinary room temperatures. Reaction periods of up to 8 hours or more at room temperature can be used.

Suitable hydrocarbylmagnesium halides include alkylmagnesium chlorides and bromides, such as ethylmagnesium chloride, propylmagnesium chloride, butylmagnesium chloride, butylmagnesium bromide, isobutylmagnesium chloride, pentylmagnesium chloride, heptylmagnesium bromide, octylmagnesium chloride, and the like. Cycloalkyl and aryl Grignard reagents such as phenylmagnesium chloride can also be used. Alkylmagnesium chlorides are preferred. Grignard reagents are often regarded as containing a complex of RMgX or a complex of $R_2Mg$ and $MgX_2$ in equilibrium with $R_2Mg$ and $MgX_2$. Thus the terms organomagnesium halide and terms of like import (e.g., hydrocarbylmagnesium halide, alkylmagnesium halide, etc.) are intended to encompass the materials commonly known as Grignard reagents, whatever their precise chemical structure or configuration may be.

Upon completion of the above treatment with the Grignard reagent, the particulate or powdery product is separated and recovered from the liquid phase by filtration or other suitable solids-liquid physical separation technique such as centrifugation or decantation, and washed with an anhydrous, oxygen-free inert diluent such as hexane. Then the product is re-suspended in an anhydrous, oxygen-free inert liquid, such as a paraffinic or cycloparaffinic hydrocarbon, preferably a low boiling hydrocarbon such as hexane, and treated with boron trihalide, preferably by bubbling boron trifluoride through the suspension at ordinary room temperature and atmospheric pressure for a suitable period of time, e.g., up to 5 or 6 hours or more. The resultant product of this invention can be separated from the liquid phase, if desired, by filtration or other suitable solids-liquid physical separation technique such as centrifugation or decantation, and washed with anhydrous, oxygen-free inert diluent such as hexane. The product can be dried under vacuum at room temperature or slightly elevated temperature (e.g., up to 65° C.) and stored under anhydrous oxygen-free conditions such as under a vacuum or under a dry inert gas such as nitrogen or argon. Alternatively the product may be kept in an anhydrous, inert liquid such as a paraffinic or cycloparaffinic hydrocarbon (e.g., hydrogenated alpha-olefin oligomer) which can be used a medium in which the oligomerization reaction is to be conducted.

If all of the hydroxyl groups of the pendant omega-hydroxyalkyl groups of the initial olefin polymer participate in the reaction with the organomagnesium halide, and if all of the resultant —O—Mg—X groups participate in the reaction with the boron trihalide, the complex of this invention as formed will typically have a magnesium:boron:halide:oxygen atom ratio of 1:1:4:1, respectively. It will be appreciated however that not all of the hydroxyl groups need participate either of the reactions, that not all of the groups that are reacted with the organomagnesium halide need react with the boron trihalide, and that the boron trihalide can react with some or all of the hydroxyl groups that have not reacted with the organomagnesium halide. Consequently as long as the polymer contains at least one and preferably a plurality of pendant groups containing a moiety composed of one atom of magnesium, one atom of boron, four atoms of halide and one atom of oxygen—a moiety which for convenience may be depicted as —O—Mg—X—$BX_3$— such polymer constitutes a composition of this invention.

Preferably at least 50%, and more preferably substantially all (i.e., at least 90% of the initial hydroxyl groups on the polymer will have been converted into such moieties.

A few illustrative complexes of this invention are tabulated below with reference to the reactants used for producing them:

| Polymer Reactant | Grignard Reagent | $BX_3$ |
|---|---|---|
| poly(propylene-co-1-hexen-6-ol) | BuMgCl | $BF_3$ |
| poly(propylene-co-1-hexen-6-ol) | AmMgCl | $BCl_3$ |
| poly(propylene-co-1-hepten-7-ol) | BuMgCl | $BF_3$ |
| poly(propylene-co-1-octen-8-ol) | iso-PrMgCl | $BF_3$ |
| poly(propylene-co-1-nonen-9-ol) | BuMgCl | $BCl_3$ |
| poly(propylene-co-1-decen-10-ol) | iso-BuMgCl | $BF_3$ |
| poly(1-butene-co-1-hexen-6-ol) | BuMgBr | $BF_3$ |
| poly(1-pentene-co-1-octen-8-ol) | iso-AmMgCl | $BCl_3$ |
| poly(1-octene-co-1-penten-5-ol) | iso-BuMgBr | $BF_3$ |

Oligomerization Reaction

In conducting the oligomerization process of this invention, oligomerization is effected by contacting the monomer(s) with a catalytic amount of the catalyst system. Typical catalytic amounts fall in the range of about 0.5% to about 30% of the weight of the monomer to be oligomerized. Preferably the catalyst system is used in the range of about 1% to about 15% of the weight of the 1-olefin monomer. Oligomerization temperatures are typically in the range of about 0 to about 80° C., and preferably are in the range of about 20 to about 60° C. Thus in conducting the oligomerization reactions of this invention at least a substantial portion of each individual reaction (e.g., at least for one-half of the total reaction period) the oligomerization reaction is performed at one or more temperatures in the foregoing ranges. To ensure intimate contact between the liquid oligomer and heterogeneous catalyst system, the reaction mixture can be agitated during the reaction, or the liquid phase can be passed through a bed of the catalyst system. Reaction times will vary depending on the type of product desired and reaction conditions used. Generally speaking reaction times will fall in the range of about 0.25 to about 3 hours. However departures from this range are permissible whenever deemed necessary or desirable, and are within the scope of this invention.

The oligomerization reaction is typically conducted at about atmospheric pressure, but super-atmospheric pressures can be used, if desired. Normally it is unnecessary to exceed pressures of about 100 psig. If it is desired to monitor the progress of the reaction, samples of the oligomerization mixtures can be taken at suitable periods during the course of the reaction and subjected to gas chromatographic (GC) analysis. The reaction can be conducted in a single stirred reactor or in a series of reactors. Alternatively, the reactor may contain a bed of the catalyst through which the liquid phase is continuously passed, or circulated in a closed loop.

To terminate the oligomerization reaction, the reaction mixture is simply separated from the heterogeneous catalyst for further processing such as distillation and/or hydrogenation. Unreacted olefin can be recovered and recycled.

As indicated above, because a heterogeneous catalyst is used in the process, the alpha-olefin oligomers can be in a series of two or more separate oligomerization reactions wherein the same solid polymer component of the catalyst is used over and over again. Thus in one of its embodiments this invention provides a process which comprises:

a) conducting a first or initial reaction of a series of separate oligomerization reactions by contacting at least one oligomerizable 1-olefin having in the range of about 6 to about 20, preferably about 8 to about 14, most preferably about 8 to about 12 carbon atoms per molecule, with a catalyst system formed from (i) a solid olefin polymer having a linear backbone and a plurality of pendant omega-hydroxyalkyl groups, (ii) an organomagnesium halide, and (iii) a boron trihalide, whereby the oligomerization results in a reaction mixture comprising a liquid alpha-olefin oligomer phase and a solids phase comprising solid olefin polymer catalyst residue;

b) separating the liquid phase and said solids phase from each other; and c) conducting another such reaction by contacting least one oligomerizable 1-olefin having in the range of about 6 to about 20, preferably about 8 to about 14, most preferably about 8 to about 12 carbon atoms per molecule with a catalyst system formed from the separated solids phase from the preceding reaction. A fresh charge of boron trihalide is completely unnecessary, at least during the extended periods of time during which the catalyst retains suitable catalytic activity. However, a fresh charge of boron trihalide can be introduced into the mixture at any suitable time, if desired.

Thus a series of 5, 10, 15 or more successive separate batch oligomerization reactions can be performed in which after the end of each reaction the liquid phase and the solids phase are separated from each other, and the solids phase is reused as the catalyst together with a fresh charge of an oligomerizable 1-olefin in conducting the next oligomerization reaction of that series of reactions. The 1-olefin can of course be varied from one run to the next.

Solvents or reaction diluents such as suitable paraffinic or naphthenic oils or paraffinic, cycloparaffinic or aromatic hydrocarbons such as hexane, heptane, octane, decane, cyclohexane, toluene, xylene, etc., can be employed if desired. Excess unreacted olefin can also serve as a diluent. Whenever deemed necessary or desirable, the oligomer can be recovered from the liquid phase in which it is formed by conventional procedures such as distillation.

In order to demonstrate the beneficial results achievable by the practice of this invention, an extended series of batch-type oligomerizations of 1-octene was carried out using a preferred catalyst system of this invention, namely a system formed from poly(propylene-co-1-hexen-6-ol) ("PP—OH"), a hydrocarbon-soluble alkylmagnesium chloride, and boron trifluoride. A typical procedure for producing PP—OH involves:

(a) forming B-(5-hexen-1-yl)-9-borobicyclo[3.3.1] nonane ("hexenyl-9-BBN"), (b) copolymerizing the hexenyl-9-BBN with propylene to form poly(propylene-co-1-hexen-6-yl-9-BBN), and (c) oxidizing this boron-containing polyolefin polymer to PP—OH by use of sodium hydroxide and hydrogen peroxide.

Although full details for conducting such procedures, including the preparation of hexenyl-9-BBN, are published in patents and technical journals, illustrative procedures are given below. It is to be noted that the copolymerization described in Example 2 below is performed using a new continuous process that gives superior results as compared to prior batch-type polymerizations. Synthesis details and oligomerization procedures and results are illustrated by the following examples.

EXAMPLE 1

Preparation of Hexenyl-9-BBN

A dry 2-liter flask is equipped with a magnetic stirring bar and a connecting tube leading to a nitrogen source. The flask is thoroughly flushed with nitrogen before the injection inlet is capped with a rubber serum stopple. A slight positive pressure of nitrogen is maintained in the flask thereafter. The flask is charged via syringe with 190 mL (1.6 mol) of 1,5-hexadiene. To the stirred diene solution is then added (via syringe) 800 mL of a 0.5 molar 9-BBN-THF solution. The reaction is effected with constant stirring at room temperature. After a period of 3 hours, excess 1,5-hexadiene and THF solvent are stripped by distillation at reduced pressure. Pure hexenyl-9-BBN is obtained at 130° C. and 10 μm.

EXAMPLE 2

Copolymerization of Propylene and Hexenyl-9-BBN in a Continuous Reaction

In a typical operation, 15.477 g of hexenyl-9-BBN and 200 mL of hexane are placed in an argon filled Parr stirred pressure reactor and sealed. Then 12 g of propylene is added under $N_2$ pressure. A slurry of 1.027 g of $TiCl_3$ and 4.705 g of $AlEt_2Cl$ in 80 mL of toluene are then added under $N_2$ pressure to catalyze the copolymerization. Additional propylene is added at 30-minute intervals with 10, 8, 6 and 5 g of propylene added, respectively. After the last monomer charge, the reaction is run for an additional hour before terminating the reaction by injection of 100 mL of isopropyl alcohol. The reaction mixture is stirred for an additional ½ hour before venting the excess pressure and flushing the polymeric product with additional isopropyl alcohol. Some typical results for copolymerization of propylene and hexenyl-9-BBN using this continuous polymerization procedure are summarized in Table 1. The process produces copolymer with narrow compositional distribution and higher yield of borane monomer than previously reported procedures.

TABLE 1

| Run No. | Mol % Hexenyl-9-BBN in Feed | Mol % Hexenyl-9-BBN in Copolymer | Reaction Time, hr | Yield, % |
| --- | --- | --- | --- | --- |
| 1 | 10 | 3.5 | 3 | 62 |
| 2 | 10 | 4.2 | 5 | 75 |
| 3 | 13 | 5.0 | 3 | 65 |
| 4 | 13 | 7.8 | 5 | 72 |

EXAMPLE 3

Oxidation of Propylene/Hexenyl-9-BBN Copolymer

Propylene/hexenyl-9-BBN copolymer and 700 mL of THF are placed in a 2-liter round bottom flask equipped with septum and stirrer. To the resultant non-homogeneous slurry is added dropwise a solution of 19 g of NaOH in 100 mL of degassed water. The flask is then cooled to 0° C. before slowly adding 87.6 g of degassed 30% $H_2O_2$ solution via a double tipped needle. The reaction mixture is allowed to slowly come to room temperature before heating up to 55° C. for 6 hours. The PP—OH polymer, poly(propylene-co-1-hexen-6-ol, is then precipitated in water, squeeze dried, and placed in a slurry 500 mL of methanol. After 3 hours of vigorous stirring, approximately 75 mL of MeOH is distilled off under $N_2$ to remove boric acid-methanol azeotrope. The polymer is again precipitated in water, squeeze dried, washed with acetone, and dried under high vacuum at 45° C. Typical properties of the PP—OH polymer formed in this manner and of polypropylene homopolymer made in by the same polymerization method (Run No. 5) are summarized in Table 2. The PP—OH polymers of Run Nos. 6 and 7 of Table 2 were produced from the hexenyl-9-BBN polymers of Run Nos. 1 and 3 of Table 1, respectively. Molecular weights were determined by intrinsic viscosity as measured in a cone/plate viscometer at 135° C. in decalin solution.

TABLE 2

| Run No. | Mol % OH in Polymer | Melting Pt., °C. | Heat of Fusion, J/g | Intrinsic Viscosity | Mυ, g/mol |
|---|---|---|---|---|---|
| 5 | none | 163 | 62.5 | 2.07 | 230,000 |
| 6 | 3.5 | 161 | 54.1 | 1.78 | 183,000 |
| 7 | 5.0 | 158 | 44.6 | 1.71 | 174,000 |

Without desiring to be bound by theoretical considerations, the data in Table 2 indicate that the crystallinities, shown by melting point and heat of fusion, of the PP—OH polymers are not much different from that of the polypropylene homopolymer, which is therefore attributed to a tapered structure of the PP—OH polymer. Also, the functional groups on the side chains are concentrated at the end of the polymer chain indicating that the polypropylene units are in consecutive sequence to form crystalline phases.

EXAMPLE 4

Preparation of Complex from PP—OH, Grignard Reagent and Boron Trifluoride

Poly(propylene-co-1-hexen-6-ol (PP—OH polymer) containing 3 mol % of hexenol groups is ground to a fine powder and vacuum dried for 2 hours. In a dry nitrogen atmosphere, the dried PP—OH polymer (6 grams) is suspended in 40 mL of anhydrous, oxygen-free hexane, and then 50 mmol of butylmagnesium chloride is introduced into the slurry. The mixture is kept at room temperature for 5 hours. The resultant complex (PP—O—Mg—Cl) is in the form of powdery solids, and is separated from the liquid phase by filtration through a glass frit and washed three times with anhydrous, oxygen-free hexane. The PP—O—Mg—Cl powder is then re-suspended in 40 mL of dry, oxygen-free hexane, and while continuously stirring the mixture, boron trifluoride is introduced at atmospheric pressure over a 3-hour period. The solids are again separated by filtration using a glass frit and washed three times with anhydrous, oxygen-free hexane. The washed powdery product, PP—O—Mg—Cl—$BF_3$ complex, is dried under vacuum for several hours. A sample of a complex formed from the PP—OH, Grignard reagent and $BF_3$ in this manner was subjected to structure characterization and was found to have an Mg:B:F atom ratio of 1:1:3.

EXAMPLE 5

Oligomerization of 1-Octene with Complex from PP—OH, Grignard Reagent and Boron Trifluoride as Catalyst A series of 12 consecutive oligomerization reactions was conducted in which the same 1 gram sample of PP—O—Mg—Cl—$BF_3$ complex produced as in Example 4 was recovered by filtration after each run in a dry box and reused in the next run, a procedure that was repeated over and over again throughout the entire series. In each run powdery solid complex and 10 mL of fresh 1-octene were charged to an air-free 50 mL flask and the mixture was heated up to 60° C. for the desired reaction time. After each run the oligomer-containing reaction product was filtered to separate the catalyst complex from the liquid oligomer-containing phase for use in the next run. The separated liquid phase was distilled under vacuum to remove unreacted 1-octene monomer. Elemental analysis of the recovered catalyst after the last run of the series showed that almost no change in $BF_3$ concentration in the catalyst occurred after 12 reaction cycles. Table 3 summarizes the conditions used and the results obtained in these 12 runs. Table 4 summarizes analytical data concerning the composition of some of the oligomers formed in these runs.

TABLE 3

| Run No. | Reaction Temp., °C. | Reaction Time, hr. | Product Yield, g | Conversion, % |
|---|---|---|---|---|
| 1 | 60 | 2 | 1.62 | 22.7 |
| 2 | 60 | 2 | 1.84 | 25.7 |
| 3 | 60 | 2 | 1.74 | 24.3 |
| 4 | 60 | 2 | 1.78 | 24.9 |
| 5 | 60 | 3 | 2.45 | 34.2 |
| 6 | 60 | 4 | 3.04 | 42.5 |
| 7 | 60 | 2 | 1.72 | 24.1 |
| 8 | 60 | 2 | 1.85 | 25.8 |
| 9 | 60 | 2 | 1.74 | 24.3 |
| 10 | 60 | 2 | 1.80 | 25.1 |
| 11 | 60 | 3 | 2.29 | 32.0 |
| 12 | 60 | 4 | 3.10 | 43.3 |

TABLE 4

| Run No. | Dimer, % | Trimer, % | Tetramer, % | Pentamer, % |
|---|---|---|---|---|
| 3 | 55.5 | 42.5 | 2.0 | none |
| 8 | 58.3 | 40.7 | 1.0 | none |

The entire disclosure of each and every U.S. patent and each and every technical publication referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of oligomerizing at least one oligomerizable 1-olefin having in the range of about 6 to about 20 carbon atoms per molecule which comprises (a) contacting said 1-olefin with a solid catalyst consisting essentially of a complex formed from (i) a solid olefin polymer having a linear backbone and a plurality of pendant omega-hydroxyalkyl groups, (ii) an organomagnesium halide, and (iii) a boron trihalide, with the catalyst complex at a level of about 0.5% to about 30% by weight of the oligomerizable 1-olefin and at a temperature of about 0° C. to about 80° C. such that a liquid oligomerization product is formed, and (b) separating the liquid oligomerization product from the solid catalyst complex, and (c) re-using the solid catalyst complex from (b) in (a).

2. A process according to claim 1 wherein said organomagnesium halide is a hydrocarbylmagnesium chloride and said boron trihalide is boron trifluoride.

3. A process according to claim 1 wherein said solid olefin polymer used in forming the complex is a poly(1-alkene-co-1-alken-ō-ol) polymer in which the alkene units can be the same or different and contain 3 to about 10 carbon atoms each and the 1-alken-ō-ol units contain 6 to about 12 carbon atoms each.

4. A process according to claim 1 wherein said oligomerizable 1-olefin is at least one oligomerizable 1-olefin having in the range of about 8 to about 14 carbon atoms per molecule, wherein said solid olefin polymer used in forming the complex is a poly(propylene-co-1-alken-ω-ol) polymer in which the 1-alken-ω-ol units contain 6 to about 12 carbon atoms each, wherein said organomagnesium halide is a hydrocarbylmagnesium chloride and wherein the boron trihalide is boron trifluoride.

5. A process according to claim 4 wherein said 1-olefin is a linear 1-olefin.

6. A process of preparing alpha-olefin oligomer in a series of two or more separate oligomerization reactions which comprises:
   a) conducting a first oligomerization reaction by contacting at least one oligomerizable 1-olefin having in the range of about 6 to about 20 carbon atoms per molecule with a solid catalyst consisting essentially of a complex formed from (i) a solid olefin polymer having a linear backbone and a plurality of pendant omega-hydroxyalkyl groups, (ii) an organomagnesium halide and (iii) a boron trihalide, whereby the oligomerization results in a reaction mixture comprising a liquid alpha-olefin oligomer phase and a solids phase comprising said olefin polymer catalyst residue; with the catalyst complex at a level of about 0.5% to about 30% by weight of the oligomerizable 1-olefin and at a temperature of about 0° C. to about 80° C.;
   b) separating said liquid phase and said solids phase from each other; and
   c) conducting another said reaction by contacting at least one oligomerizable 1-olefin having in the range of about 6 to about 20 carbon atoms per molecule with said solids phase as the aforesaid catalyst complex, with the catalyst complex at a level of about 0.15% to about 30% by weight of the oligomerizable 1-olefin and at a temperature of about 0° C. to about 80° C.;
with the oligomerization product formed in each of steps (a) and (c) being liquid.

7. A process according to claim 6 wherein said organomagnesium halide is a hydrocarbylmagnesium chloride and said boron trihalide is boron trifluoride.

8. A process according to claim 6 wherein said series of separate oligomerization reactions comprises at least 5 successive separate oligomerization reactions in which after the end of each reaction said liquid phase and said solids phase are separated from each other and said solids phase is used together with a fresh charge of at least one oligomerizable 1-olefin having in the range of about 6 to about 20 carbon atoms per molecule in conducting the next oligomerization reaction.

9. A process according to claim 6 wherein in each said separate oligomerization reaction said oligomerizable 1-olefin is at least one oligomerizable 1-olefin having in the range of about 8 to about 14 carbon atoms per molecule, wherein said organomagnesium halide is a hydrocarbylmagnesium chloride, and wherein said boron trihalide is boron trifluoride.

10. A process according to claim 6 wherein said solid olefin polymer used in forming the complex is a poly(1-alkene-co-1-alken-ω-ol) polymer in which the alkene units can be the same or different and contain 3 to about 10 carbon atoms each and wherein the 1-alken-ω-ol units contain 6 to about 12 carbon atoms each.

11. A process according to claim 6 wherein said oligomerizable 1-olefin in each of said two or more separate oligomerization reactions is at least one oligomerizable 1-olefin having in the range of about 8 to about 14 carbon atoms per molecule, wherein said solid olefin polymer used in forming said complex is a poly(propylene-co-1-alken-ω-ol) polymer in which the 1-alken-ω-ol units contain 6 to about 12 carbon atoms each, and wherein the boron trihalide is boron trifluoride.

12. A process according to claim 6 wherein said 1-olefin in a) and c) thereof is linear 1-olefin.

13. A process according to claim 6 wherein said solid olefin polymer used in forming said complex is poly(propylene-co-(1-hexen-6-ol).

14. A process according to claim 1 wherein said 1-olefin in a) and c) thereof is linear 1-olefin.

15. A process according to claim 14 wherein said poly(propylene-co-1-alken-ω-ol) polymer is poly(propylene-co-(1-hexen-6-ol).

16. A process according to claim 15 wherein said oligomerizable 1-olefin is predominately one or more $C_8$–$C_{12}$ linear 1-olefins.

17. A process according to claim 10 wherein said series of separate oligomerization reactions comprises at least 5 successive separate oligomerization reactions in which after the end of each reaction said liquid phase and said solids phase are separated from each other and said solids phase is used together with a fresh charge of said oligomerizable 1-olefin in conducting the next oligomerization reaction.

18. A process according to claim 10 wherein said series of separate oligomerization reactions comprises at least 10 successive separate oligomerization reactions in which after the end of each reaction said liquid phase and said solids phase are separated from each other and said solids phase is used together with a fresh charge of said oligomerizable 1-olefin in conducting the next oligomerization reaction, and wherein said oligomerizable 1-olefin is predominately one or more $C_8$–$C_{12}$ linear 1-olefins.

19. A process according to claim 18 wherein said linear 1-olefin is 1-octene, and wherein said poly(propylene-co-1-alken-ω-ol) polymer is poly(propylene-co-(1-hexen-6-ol).

20. A process according to claim 10 wherein said series of separate oligomerization reactions comprises at least 12 successive separate oligomerization reactions in which after the end of each reaction said liquid phase and said solids phase are separated from each other and said solids phase is used together with a fresh charge of boron trifluoride and a fresh charge of said oligomerizable 1-olefin in conducting the next oligomerization reaction, wherein said oligomerizable 1-olefin is predominately one or more $C_8$–$C_{12}$ linear 1-olefins, wherein said poly(propylene-co-1-alken-ω-ol) polymer is poly(propylene-co-(1-hexen-6-ol), wherein said organomagnesium halide is a hydrocarbylmagnesium chloride.

* * * * *